United States Patent
Virágh et al.

(10) Patent No.: US 8,221,788 B2
(45) Date of Patent: Jul. 17, 2012

(54) PHARMACEUTICAL COMPOSITIONS CONTAINING ROSUVASTATIN CALCIUM

(75) Inventors: Mária Virágh, Budapest (HU); Ildikó Monostori, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 370 days.

(21) Appl. No.: 12/441,396

(22) PCT Filed: Sep. 11, 2007

(86) PCT No.: PCT/HU2007/000082
§ 371 (c)(1), (2), (4) Date: Jul. 15, 2009

(87) PCT Pub. No.: WO2008/035128
PCT Pub. Date: Mar. 27, 2008

(65) Prior Publication Data
US 2009/0297599 A1    Dec. 3, 2009

(30) Foreign Application Priority Data
Sep. 18, 2006    (HU) .................................... 0600728

(51) Int. Cl.
*A61K 9/20* (2006.01)
*A61K 9/28* (2006.01)
*A61K 31/19* (2006.01)
*A01N 43/54* (2006.01)
*A01N 37/12* (2006.01)
*A01N 37/44* (2006.01)
*A01N 37/00* (2006.01)
*A01N 37/10* (2006.01)
*C07D 239/02* (2006.01)

(52) U.S. Cl. ........ 424/465; 424/474; 514/275; 514/557; 514/561; 514/562; 514/567; 514/570; 544/322; 544/330

(58) Field of Classification Search .................. 424/465, 424/474; 514/275, 557, 561, 562, 567, 570; 544/322, 330
See application file for complete search history.

(56) References Cited

U.S. PATENT DOCUMENTS

| | | | |
|---|---|---|---|
| 5,180,589 A * | 1/1993 | Joshi et al. ..................... | 424/465 |
| 5,260,440 A | 11/1993 | Hirai et al. ..................... | 544/233 |
| 6,316,460 B1 | 11/2001 | Creekmore et al. ........... | 514/275 |
| 6,548,513 B1 | 4/2003 | Creekmore et al. .......... | 514/275 |
| 2003/0031720 A1 | 2/2003 | Laich et al. ................... | 424/489 |
| 2003/0175338 A1 | 9/2003 | Singh et al. ................... | 424/465 |
| 2003/0211151 A1 | 11/2003 | Tillyer et al. ................. | 424/468 |
| 2004/0072894 A1 | 4/2004 | Kerc .............................. | 514/423 |
| 2004/0167085 A1 | 8/2004 | Hedge et al. ................... | 514/42 |
| 2007/0202159 A1 * | 8/2007 | Mathur et al. ................ | 424/451 |

FOREIGN PATENT DOCUMENTS

| WO | WO-2004071402 | 8/2004 |
| WO | WO 2006084474 A2 * | 8/2006 |

* cited by examiner

*Primary Examiner* — Johann Richter
*Assistant Examiner* — Jane C Oswecki
(74) *Attorney, Agent, or Firm* — Jonathan Myers; Andrew Wilford

(57) ABSTRACT

A pharmaceutical composition is disclosed containing amorphous rosuvastatin calcium and at least one of the following stabilizing agents: magnesium hydroxide, calcium acetate, calcium gluconate, calcium glycerophosphate, or aluminum hydroxide, together with at least one pharmaceutically acceptable excipient.

9 Claims, No Drawings

PHARMACEUTICAL COMPOSITIONS CONTAINING ROSUVASTATIN CALCIUM

CROSS REFERENCE TO RELATED APPLICATIONS

This application is the US National Phase of PCT/HU2007/000082 filed 11 Sep. 2007 and claiming the benefit of the priority of Hungarian Patent Application P06 00728 filed 18 Sep. 2006.

FIELD OF THE INVENTION

The present invention relates to a novel pharmaceutical composition containing rosuvastatin calcium as active ingredient and magnesium hydroxide and/or calcium acetate or calcium gluconate or calcium glycerophosphate or aluminum hydroxide as stabilizing agent and process for the manufacturing thereof.

BACKGROUND OF THE INVENTION

It is known that the rosuvastatin {(E)-7-[4-(4-fluorophenyl)-6-isopropyl-2-[methyl(methylsulfonyl)amino]pyrimidin-5-yl](3R,5S)3,5-dihydroxyhept-6-enoic acid calcium salt} as an active ingredient and the process for the synthesis thereof were first described in the patent EP 521,471.

It is also known that the marketed (under Crestor trade name) pharmaceutical composition is described among others in the WO 01/54668, WO 01/54669 or U.S. Pat. No. 6,316,460 patent specifications. According to these descriptions manufacturing of stable, solid pharmaceutical composition containing rosuvastatin can not be accomplished only by using pH adjuvant compounds, but the presence of inorganic salts of multivalent metals is also required to prevent the formation of lactone and oxidation decomposition products. In the pharmaceutical composition inorganic salts of multivalent metals (Ca, Mg, Zn, Al, Fe and the combinations thereof) are used as stabilizing additives such as aluminum, magnesium metasilicate, tribasic calcium phosphate, tribasic magnesium phosphate and tribasic aluminum phosphate. The marketed (under Crestor trade name) pharmaceutical composition contains tribasic calcium phosphate as stabilizing agent.

There are several patent applications and specifications dealing with the formulation problems of HMG-CoA reductase inhibitors, namely statins, in general. It is known from the literature that from among HMG-CoA reductase inhibitor, lipid-lowering drugs several compounds are sensitive to the properties of the micro-environment of the composition, in fact to light, to heat and humidity. The following patent specifications describe pharmaceutical compositions containing statins, among others rosuvastatin.

The WO 02/089788 describes statin containing pharmaceutical compositions the stability of which are provided by addition of amino sugars (for example N-methyl-glucoseamine). According to the description the advantage of the amino sugars versus inorganic alkali-earth metal salts is that they do not irritate the mucosa in the intestines.

The WO 00/53173 describes delayed-release pharmaceutical compositions containing statins as active ingredients, in which the release of the active ingredient in the stomach and the lactone formation under acidic conditions are prevented by special gel structure and enterically coated dosage form.

The WO 01/62230 describes a mannitol based granulate, in which the active ingredient statins are dissolved in NaOH solution and are added together with the granulating solution to the pharmaceutical dosage form.

According to the state of the art mentioned above there is a need for producing statin—in our case rosuvastatin—containing stable pharmaceutical compositions, which are easy to formulate.

OBJECT OF THE INVENTION

The aim of the present invention is to develop a stable pharmaceutical composition containing rosuvastatin calcium, the manufacturing of which is simple and the elaborated compositions make possible the dose-proportional dosage of the active ingredient.

SUMMARY OF THE INVENTION

During our experiments surprisingly it was found, that a stable pharmaceutical composition can be produced by using magnesium hydroxide and/or calcium acetate or calcium gluconate or calcium glycerophosphate or aluminum hydroxide as pharmaceutical excipients. In addition to this the possible compositions of the pharmaceutical dosage forms are defined in such a way that those are suitable for the dose-proportional formulation of the product family.

The present invention relates to a novel pharmaceutical composition containing amorphous rosuvastatin calcium and magnesium hydroxide and/or calcium acetate or calcium gluconate or calcium glycerophosphate or aluminum hydroxide as stabilizer and one or more pharmaceutically acceptable excipients.

According to the present invention the pharmaceutical composition preferably contains magnesium hydroxide and/or calcium acetate as stabilizing additive.

According to the present invention the pharmaceutical composition contains diluent and/or binder and/or disintegrant and/or lubricant and/or film-coating materials as pharmaceutically acceptable excipients and in given case further excipients.

The pharmaceutical composition contains lactose and/or microcrystalline cellulose as diluent, povidone as binder, crospovidone as disintegrant and magnesium stearate as lubricant.

The new pharmaceutical composition is film-coated.

The present invention also relates to the process for the production of the pharmaceutical composition according to our invention, which consists of the following steps: sieving the active ingredient and the excipients, blending the active ingredient, the stabilizing additive, diluent, binder, disintegrant, adding the lubricant to the inner phase, blending the mixture, in given case adding further excipients to the mixture and compressing to tablets, finally coating the tablets.

The invention is further illustrated by the following examples.

EXAMPLES

Examples 1-8

In order to prove the stability of the pharmaceutical compositions according to our invention the stability of rosuvastatin calcium containing dosage forms of examples 1-8 was examined, which were produced by the same process using different stabilizing additives in equal amounts.

During the stress-stability study the pharmaceutical compositions were kept at 75° C. for 7 days.

TABLE 1

Composition of the pharmaceutical dosage form of Examples 1-8

| Components | Compositions of Examples (w/w %) | | | | | | | |
|---|---|---|---|---|---|---|---|---|
| | 1 | 2 | 3 | 4 | 5 | 6 | 7 | 8 |
| Rosuvastatin calcium | 6.93 | 6.93 | 6.93 | 6.93 | 6.93 | 6.93 | 6.93 | 6.93 |
| Crospovidone | 5.00 | 5.00 | 5.00 | 5.00 | 5.00 | 5.00 | 5.00 | 5.00 |
| Lactose | 45.00 | 45.00 | 45.00 | 45.00 | 45.00 | 45.00 | 45.00 | 45.00 |
| Microcrystalline cellulose | 17.00 | 17.00 | 17.00 | 17.00 | 17.00 | 17.00 | 17.00 | 17.00 |
| Magnesium stearate | 1.07 | 1.07 | 1.07 | 1.07 | 1.07 | 1.07 | 1.07 | 1.07 |
| Tribasic calcium phosphate (see: U.S. Pat. No. 6,316,460 as reference stabilizing additive) | 25.00 | — | — | — | — | — | — | — |
| Magnesium hydroxide | — | 25.00 | — | — | — | — | — | — |
| Calcium acetate | — | — | 25.00 | — | — | — | — | — |
| Trometamol | — | — | — | 25.00 | — | — | — | — |
| Calcium gluconate | — | — | — | — | 25.00 | — | — | — |
| Calcium glycerophosphate | — | — | — | — | — | 25.00 | — | — |
| Magnesium acetate | — | — | — | — | — | — | 25.00 | — |
| Aluminum hydroxide | — | — | — | — | — | — | — | 25.00 |

The above compositions (Example 1-8) were produced the following way:

The active ingredient and the excipients were sieved, the active ingredient, one of the above stabilizing additives, the diluent and the disintegrant were blended. Then the lubricant was added to the inner phase, the mixture was blended and compressed to tablets.

The results of the stress-stability study are summarized in Table 2.

TABLE 2

The results of the stability experiments of compositions 1-8

| | Results at 75° C. for 7 days | |
|---|---|---|
| Example/stabilizer | Total degradation product (%) | Lactone product (%) |
| Example 1/tribasic calcium phosphate | 0.5 | 0.3 |
| Example 2/magnesium hydroxide | 0.3 | 0.2 |
| Example 3/calcium acetate | 0.1 | 0.1 |
| Example 4/trometamol | >30 | 16.6 |
| Example 5/calcium gluconate | 0.7 | 0.4 |
| Example 6/calcium glycerophosphate | 0.2 | 0.1 |
| Example 7/magnesium acetate | >30 | 26.0 |
| Example 8/aluminum hydroxide | 1.2 | 0.5 |

According to the results of the stress-stability study of compositions 1-8 we can state that from among the examined samples degradation profile of samples containing stabilizing additives such as magnesium hydroxide, calcium acetate, calcium gluconate, calcium glycerophosphate and aluminum hydroxide was similar to the marketed product (Crestor) containing tribasic calcium phosphate as stabilizing additive. Therefore these compositions are suitable for producing stable pharmaceutical dosage forms containing amorphous rosuvastatin calcium.

According to the results magnesium acetate and trometamol used in equal amounts are not suitable for stabilizing the pharmaceutical dosage form containing amorphous rosuvastatin calcium.

The following examples describe the corpus composition and production of the dose-proportional product family (5 mg, 10 mg, 20 mg and 40 mg activity):

Example 9

| Corpus composition | Ratio (w/w %) in the composition |
|---|---|
| Rosuvastatin calcium | 6.93 |
| Lactose | 58.00 |
| Microcrystalline cellulose | 28.74 |
| Magnesium hydroxide | 5.00 |
| Crospovidone | 0.33 |
| Magnesium stearate | 1.00 |

Example 10

| Corpus composition | Ratio (w/w %) in the composition |
|---|---|
| Rosuvastatin calcium | 6.93 |
| Lactose | 55.00 |
| Microcrystalline cellulose | 27.07 |
| Calcium acetate | 5.00 |
| Crospovidone | 5.00 |
| Magnesium stearate | 1.00 |

Example 11

| Corpus composition | Ratio (w/w %) in the composition |
| --- | --- |
| Rosuvastatin calcium | 6.93 |
| Lactose | 54.00 |
| Microcrystalline cellulose | 26.57 |
| Magnesium hydroxide | 5.00 |
| Crospovidone | 5.00 |
| Povidone | 1.50 |
| Magnesium stearate | 1.00 |

Example 12

| Corpus composition | Ratio (w/w %) in the composition |
| --- | --- |
| Rosuvastatin calcium | 6.93 |
| Lactose | 55.55 |
| Microcrystalline cellulose | 29.02 |
| Magnesium hydroxide | 2.50 |
| Calcium acetate | 2.50 |
| Crospovidone | 2.50 |
| Magnesium stearate | 1.00 |

Example 13

Process for the Production of the Tablets According to Our Invention

The production of the tablets of Examples 9-12 consists of the following steps:
1. The excipients are sieved.
2. The ingredients can be homogenized by two different methods:

2a. Blending in Container Blender:

The active ingredient and the excipients of the inner phase (lactose, microcrystalline cellulose, magnesium hydroxide and/or calcium acetate, crospovidone and in case of need povidone) are blended in the homogenization equipment with 20 rpm (rotation/minute) stirring speed for 5 minutes. Then the excipient of the external phase, magnesium stearate, is added to the powder mixture and the powder mixture is blended in the container blender with 20 rpm stirring speed for 2 minutes.

2b. Blending in High-Shear Mixer:

The active ingredient and the excipients of the inner phase (lactose, microcrystalline cellulose, magnesium hydroxide and/or calcium acetate, crospovidone and in case of need povidone) are blended in two portions in high-shear mixer, first for 3 minutes, then for 4 minutes.
Setting Values:
  Stirrer: 300 rpm
  Chopper: 1050 rpm
Then the excipient of the external phase, magnesium stearate, is added to the powder mixture and the powder mixture is blended in high-shear mixer (stirrer: 300 rpm, chopper: 1050 rpm) or in the container blender (with 20 rpm stirring speed) for further 2 minutes.
3. The powder mixture homogenized with the external phase is compressed to tablets in a rotating tablet compressing machine.

Example 14

Production of Film-Coated Tablets 5 mg, 10 mg, 20 mg and 40 mg

The core tablets of Examples 9-12 are film-coated with an aqueous solution of OPADRY® II White, 85F18422. OPADRY® II White, 85F18422 is a dispersion comprising polyvinylalcohol, titanium dioxide, polyethylene glycol and talc.

The amount of the coating is ~3% of that of the individual tablets.

What we claim is:

1. A pharmaceutical composition which comprises a therapeutically effective amount of amorphous rosuvastatin calcium, at least one stabilizing additive selected from the group consisting of magnesium hydroxide, calcium acetate, calcium gluconate, calcium glycerophosphate, and aluminum hydroxide and at least one pharmaceutically acceptable excipient.

2. The pharmaceutical composition according to claim 1, wherein magnesium hydroxide is the stabilizing additive.

3. The pharmaceutical composition according to claim 1 wherein the at least one pharmaceutically acceptable excipient is selected from the group consisting of a diluent, a binder, a disintegrant, a lubricant, and a film-coating material.

4. The pharmaceutical composition according to claim 3 wherein the diluent is lactose, microcrystalline cellulose or lactose and microcrystalline cellulose.

5. The pharmaceutical composition according to claim 3 wherein the binder is povidone.

6. The pharmaceutical composition according to claim 3 wherein the disintegrant is crospovidone.

7. The pharmaceutical composition according to claim 3 wherein the lubricant is magnesium stearate.

8. The pharmaceutical composition according to claim 3 wherein the pharmaceutically acceptable excipient is a film-coating material.

9. A process for preparing the pharmaceutical composition according to claim 1, in the form of a tablet, which comprises the following steps:
   sieving the rosuvastatin calcium, the at least one stabilizing additive and the at least one pharmaceutically acceptable excipient,
   ii) homogenizing the rosuvastatin calcium, the at least one stabilizing additive, and a diluent, a binder and a disintegrant to form an inner phase,
   iii) adding a lubricant to the inner phase to form a mixture,
   iv) blending the mixture,
   v) optionally adding further excipients to the mixture and pressing the mixture into tablets, and finally
   vi) film-coating the tablets.

* * * * *